(12) United States Patent
Fan

(10) Patent No.: US 6,932,331 B1
(45) Date of Patent: Aug. 23, 2005

(54) COMBINATION OF AIR REFRESHER AND ELECTRONIC APPLIANCE HOLDING DEVICE

(76) Inventor: Eagle Fan, No.133, Cheng-Kung 6 St., Chu-Pei City, Hsinchu Hsien (TW)

( * ) Notice: Subject to any disclaimer, the term of this patent is extended or adjusted under 35 U.S.C. 154(b) by 0 days.

(21) Appl. No.: 10/782,251

(22) Filed: Feb. 18, 2004

(51) Int. Cl.$^7$ .............................................. B01F 3/04
(52) U.S. Cl. ...................... 261/30; 74/29; 261/DIG. 88
(58) Field of Search ........................... 261/24, 30, 104, 261/107, DIG. 4, DIG. 17, DIG. 88, DIG. 89, 261/DIG. 65; 239/53–57; 74/29; 422/4, 422/124

(56) References Cited

U.S. PATENT DOCUMENTS

| | | | | |
|---|---|---|---|---|
| 2,562,959 A | * | 8/1951 | Stern | 352/85 |
| 2,813,452 A | * | 11/1957 | Laube | 352/38 |
| 2,905,049 A | * | 9/1959 | Laube | 352/85 |
| 3,992,956 A | * | 11/1976 | Fischer | 74/29 |
| 4,603,030 A | * | 7/1986 | McCarthy | 472/57 |
| 4,813,344 A | * | 3/1989 | Greif | 454/156 |
| 6,085,113 A | * | 7/2000 | Fan | 455/569.1 |
| 6,161,820 A | * | 12/2000 | Wu | 261/104 |
| 6,360,083 B1 | * | 3/2002 | Fan | 455/90.1 |
| 6,783,117 B2 | * | 8/2004 | Wohrle | 261/26 |
| D499,092 S | * | 11/2004 | Fan | D14/253 |
| 2002/0158351 A1 | * | 10/2002 | Wohrle | 261/142 |

FOREIGN PATENT DOCUMENTS

JP          1-283456        * 11/1989   .................... 74/29

* cited by examiner

Primary Examiner—Richard L. Chiesa

(57) ABSTRACT

A holding device is composed of a base and a cover. An air refresher is positioned in a receiving portion of the device and an electronic appliance is clamped between two clamping plates on two sides of the device. A sliding mechanism is received in the device and includes a gear that drives a sleeve to which a core of the air refresher is connected. A fan is located in the device so as to dispense the fragrance through holes defined through the base and the cover.

10 Claims, 6 Drawing Sheets

COMBINATION OF AIR REFRESHER AND ELECTRONIC APPLIANCE HOLDING DEVICE

FIELD OF THE INVENTION

The present invention relates to a device for holding an electronic appliance and an air refresher is connected to the device.

BACKGROUND OF THE INVENTION

An air refresher is used so as to provide better smell in the car and generally the air refresher is randomly fixed on the dashboard by adhesive tape. The adhesive tape cannot well position the air refresher that is a container with liquid received therein. Besides, the tape leaves dirty residue on the dashboard, which is difficult to remove. In addition, many drivers use a holding device for holding a cellular phone and the holding device is clamped to the dashboard of the car so that there is no place for the air refresher. Unfortunately, the conventional holding device does not include a feature to accommodate the air refresher.

Therefore, it is desired to have a holding device that holds an electronic appliance such as a cellular phone and an air refresher is connected to the holding device.

SUMMARY OF THE INVENTION

In accordance with an aspect of the present invention, there is provided an air refresher holding device, which comprises an air refresher engaged with a lower end of the holding device that is composed of a base and a cover. A sliding mechanism comprises a gear and a sleeve that has teeth matched with the gear so that the sleeve is moved by rotating the gear. A first clamping plate movably inserted in a side of the device has a rack portion on a side thereof and a pawl member is disengageably engaged with the rack portion so as to hold the first clamping plate in position. A plurality of first holes is defined through the base and the cover. A path is located in the base and the sliding mechanism is received in the path and extended to a position where the holes are defined. A second clamping plate is connected to the other side of the device so that an electronic appliance is clamped between the two clamping plates.

The present invention will become more obvious from the following description when taken in connection with the accompanying drawings, which show, for purposes of illustration only, a preferred embodiment in accordance with the present invention.

DETAILED DESCRIPTION OF THE PREFERRED EMBODIMENT

Figure 1:
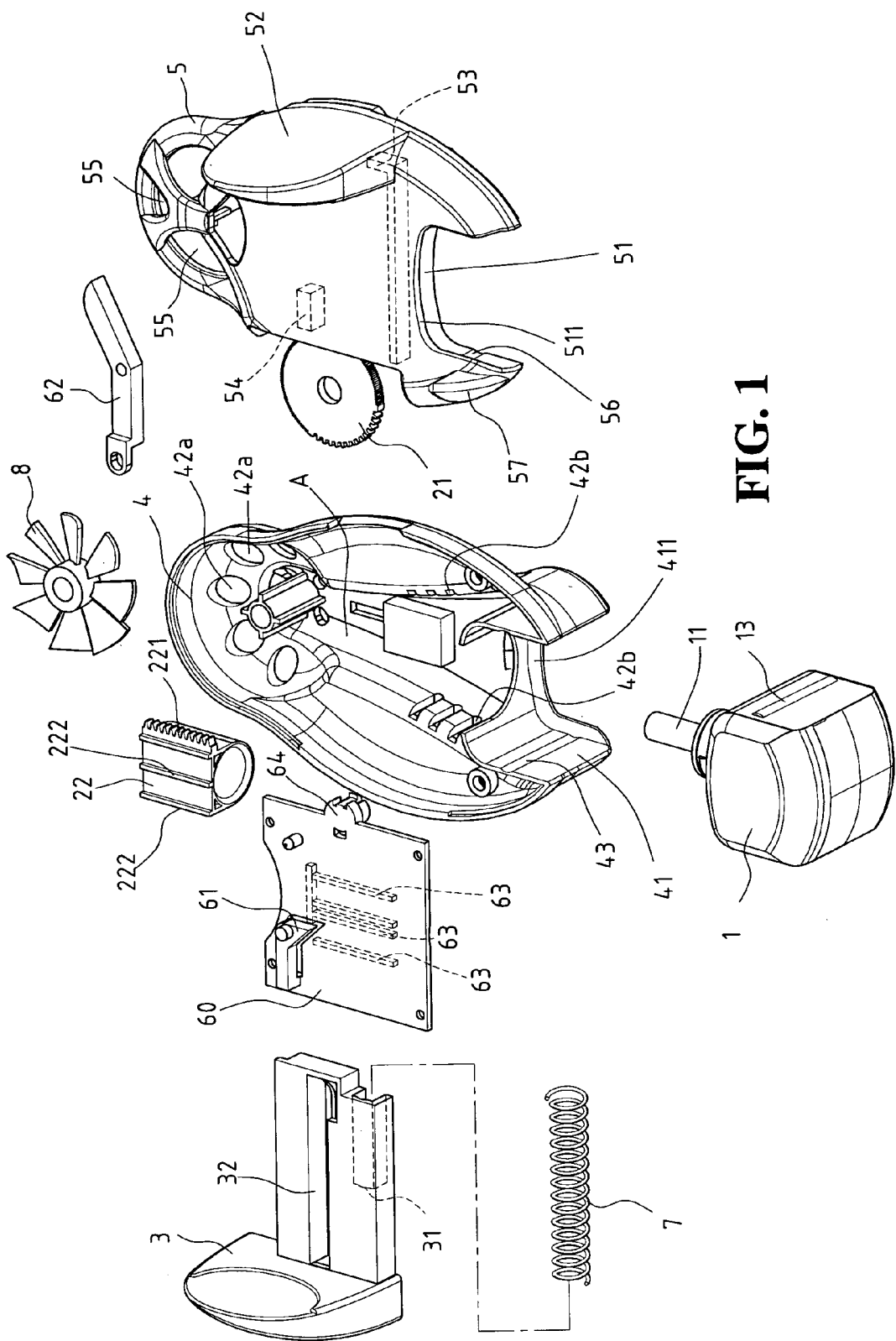
FIG. 1 is an exploded view of a holding device in accordance with the present invention.
Figure 2:
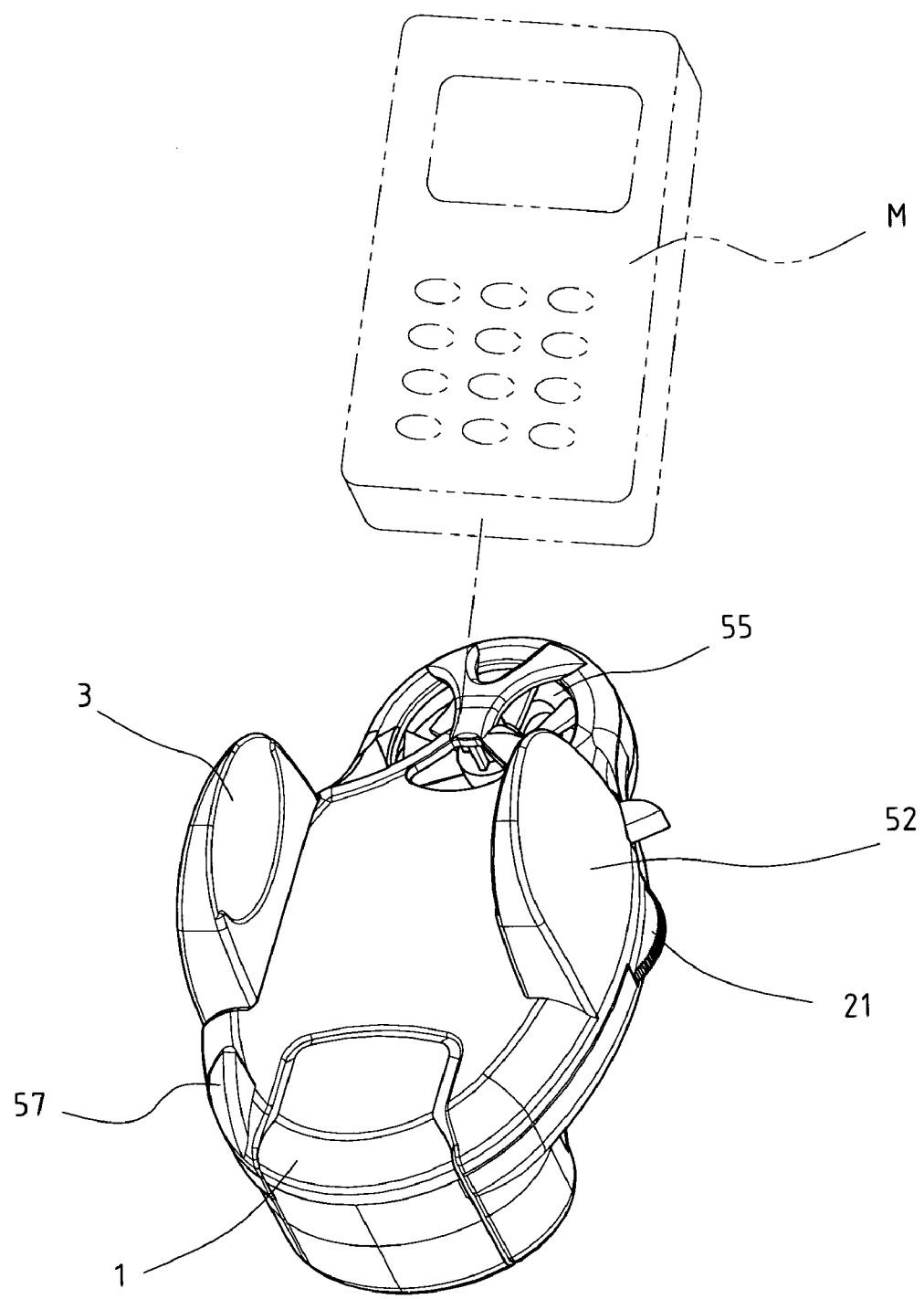
FIG. 2 shows a cellular phone to be clamped by two clamping plates of the holding device of the present invention.
Figure 3:
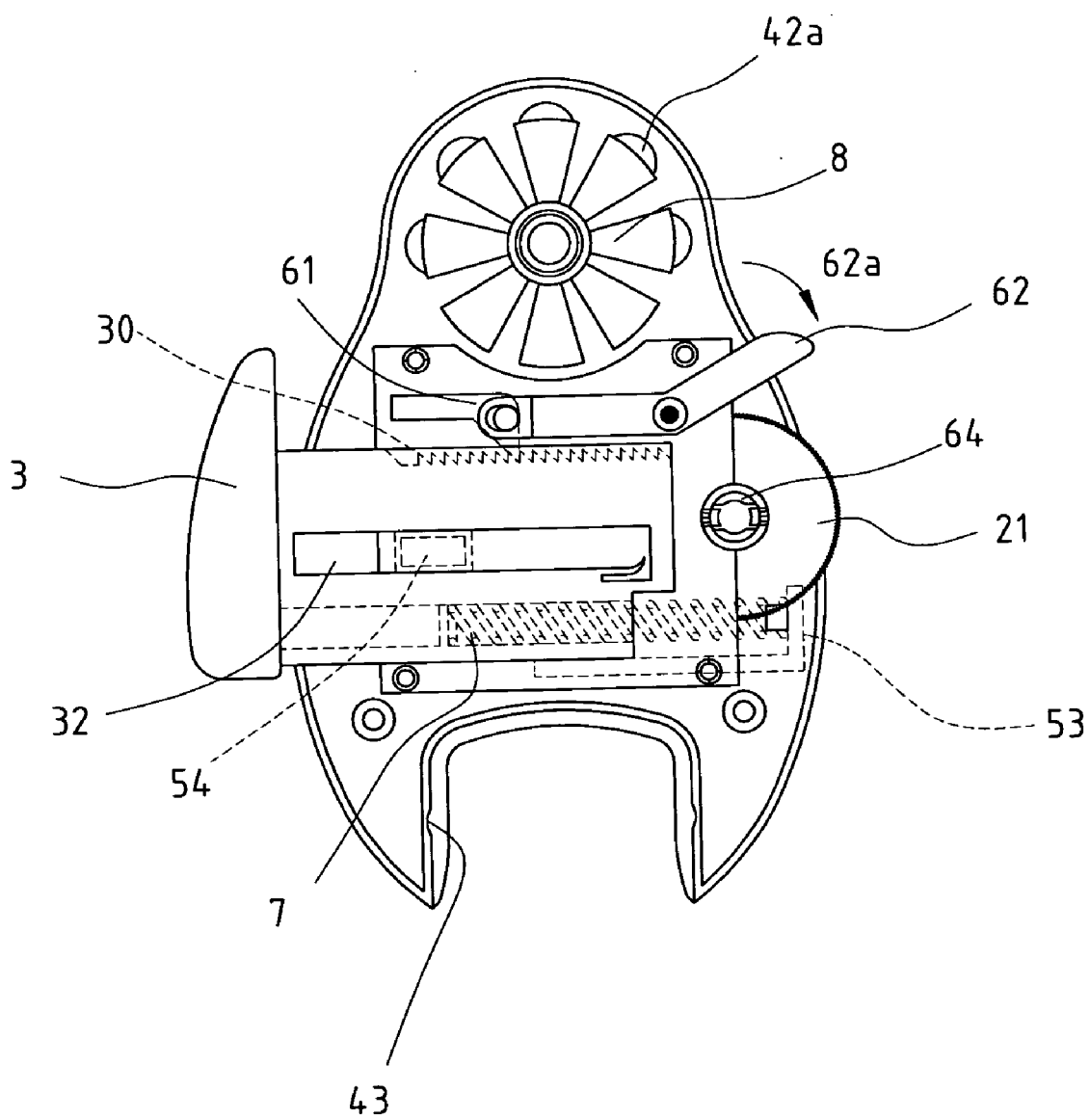
FIG. 3 shows that a first clamping plate is positioned by the pawl member.

Referring to the drawings and in particular FIGS. 1 to 3, an air refresher holding device of the present invention comprises a base 4 having a first receiving portion 41 defined in an end thereof and a path "A" is defined in an interior of the base 4 so that a sliding mechanism 2 is located in that path "A". The cover 5 is mounted onto the base 4 and includes a second receiving portion 51 that is located in alignment with the first receiving portion 41 such that an air refresher 1 is received therein. The cover 5 has a support member 57 located on an end thereof and located beside the second receiving portion 51.

The air refresher 1 includes two ridges 13 on two sides thereof and two grooves 43, 56 are respectively defined in two insides of the first and second receiving portions 41, 51, so that the ridges 13 are engaged with the grooves 43, 56. In addition, each of the first receiving portion 41 and the second receiving portion 51 has a flange 411, 511 so as to clamp the air refresher 1 therebetween. A plurality of first holes 42a is defined through the base 4 and the path "A" is extended to a position where the first holes 42a are defined. A plurality of second holes 55 is defined through the cover 5 and located corresponding to the first holes 42a. The base 4 further includes a plurality of third holes 42b that are located on two sides of the path "A".

Figure 5:
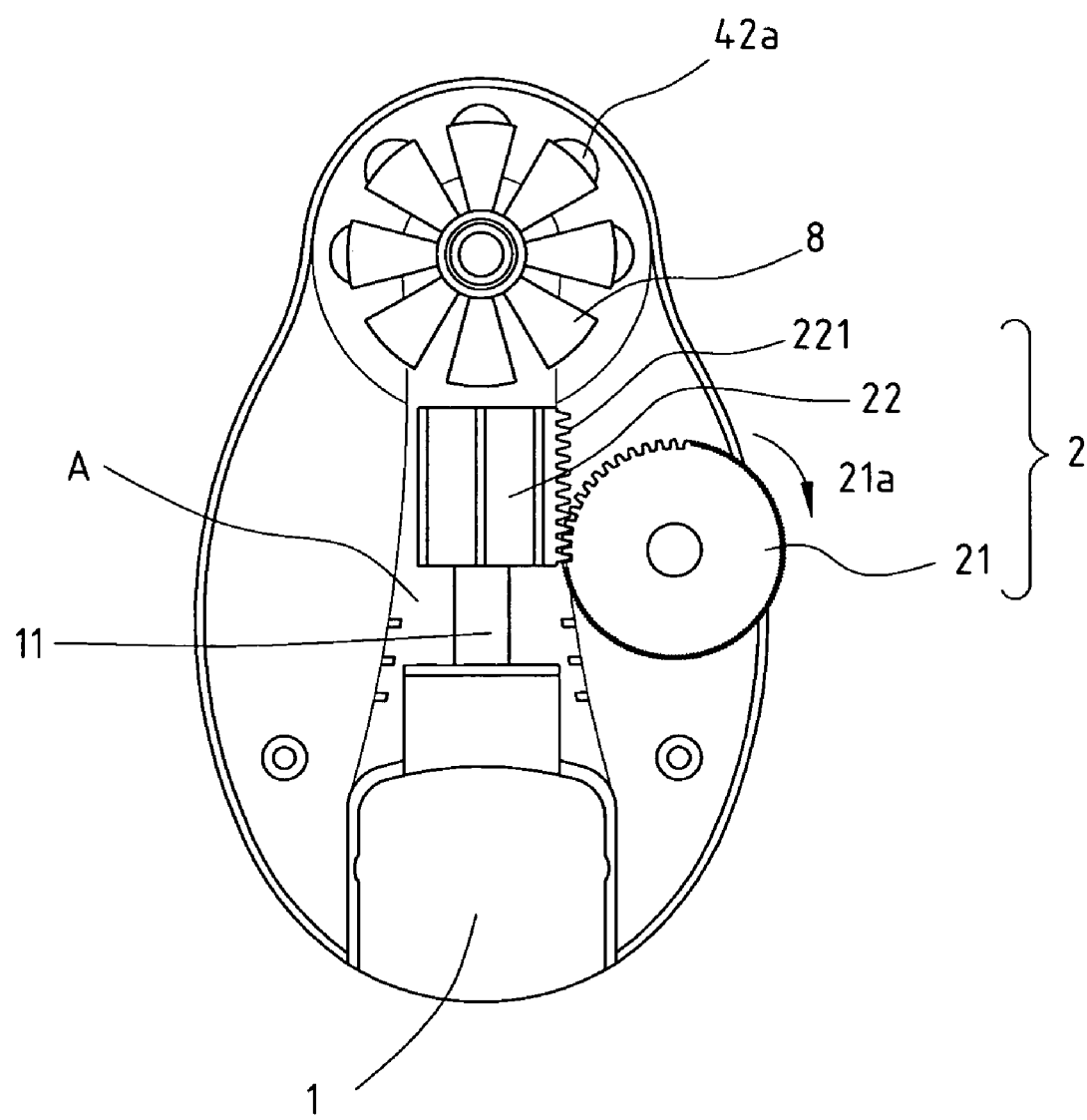
FIG. 5 shows that a sleeve together with a core of the air refresher are moved by rotating the gear.
Figure 6:
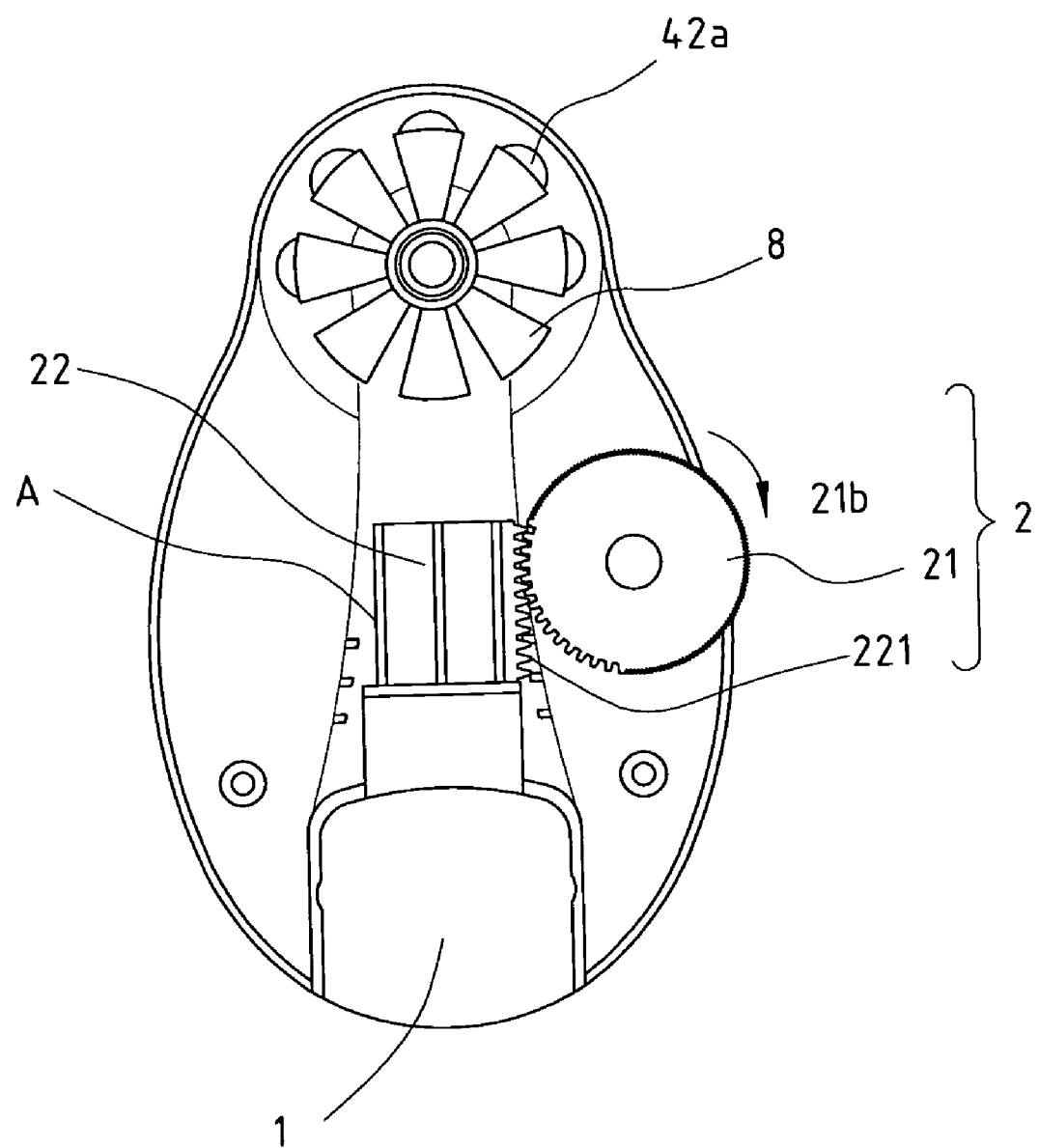
FIG. 6 shows that the sleeve together with the core of the air refresher are moved in opposite direction by rotating the gear.

The sliding mechanism 2 comprises a gear 21 and a sleeve 22 that has teeth 221 matched with the gear 21. The air refresher 1 includes a core 11 for sucking the fragrance in the air refresher 1 and the core 11 is inserted in the sleeve 22. The sleeve 22 and the core 11 are moved by rotating the gear 21 in a direction 21a as shown in FIG. 5 to pull the core 11 so that the fragrance can be dispensed through the holes 42a, 42b and 55. On the contrary, as shown in FIG. 6, when rotating the gear 21 in a direction 21b, the core 11 is totally received in the bottle of the air refresher 1. A fan 8 is located between the base 4 and the cover 5, and the first holes 42a and the second holes 55 are located on two sides of the fan 8 so that the fragrance is dispensed from the holes by the fan 8.

A first clamping plate 3 has a rack portion 30 on a side thereof and is inserted in a side of the device. A chamber 31 is defined in an underside thereof and the cover 5 has a stop wall 33. A spring 7 has an end received in the chamber 31 and the other end of the spring 7 contacts against the stop wall 33. The spring 7 provides a force to push the first clamping plate 3 outward. A second clamping plate 52 is connected to a side of the cover 5 and located in opposite to the first clamping plate 3. The cover 5 includes a block 54 and the first clamping plate 3 includes a slot 32 in which the block 54 is slidably engaged, so that the first clamping plate 3 will not drop from the device. A cellular phone "M" can be clamped between the first clamping plate 3 and the second clamping plate 52, and the cellular phone "M" are supported on the support member 57.

Figure 4:
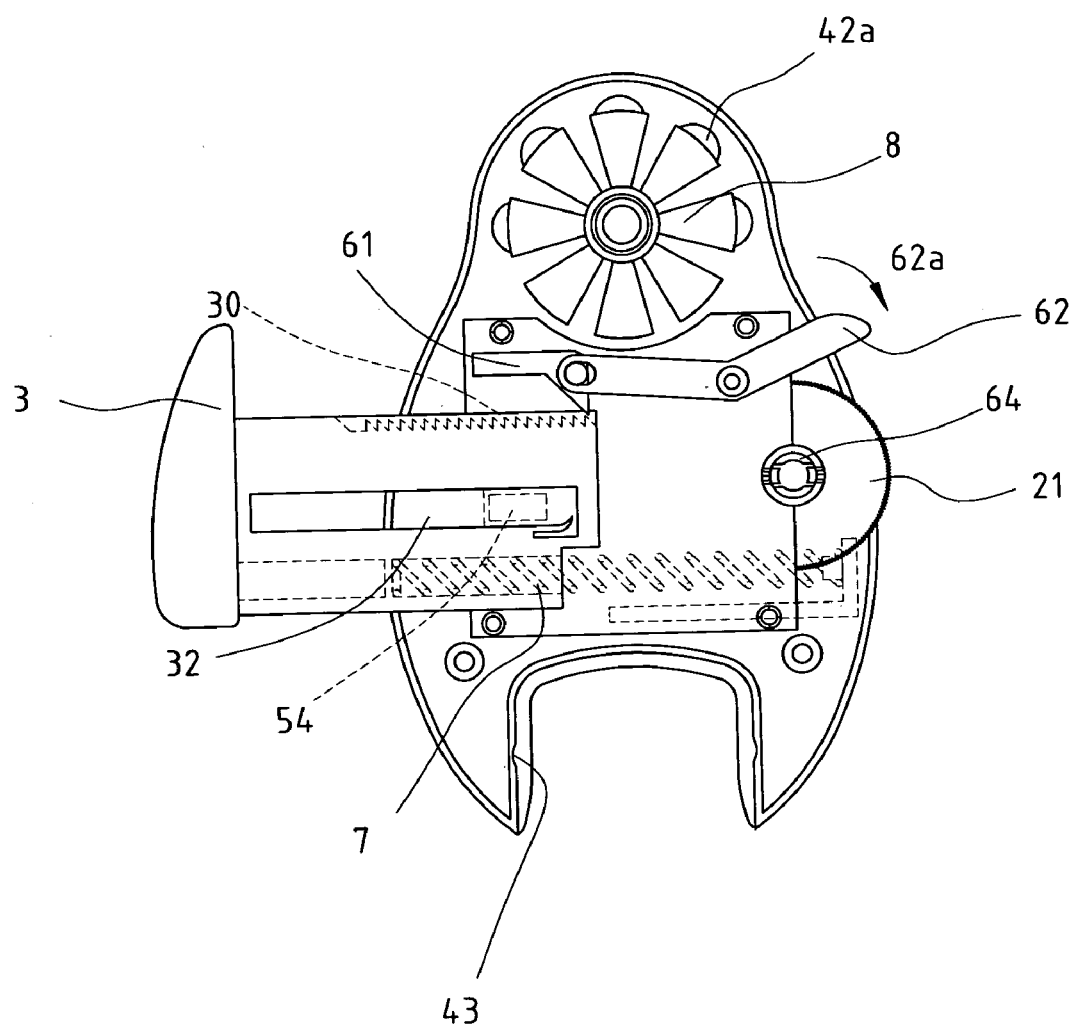
FIG. 4 shows that the first clamping plate is moved outward when pivoting the pushing rod.

A board 60 is located in the device and a pawl member 61 is integrally connected to a board 60 that has a protrusion 64 to which a center of the gear 21 is connected. The pawl member 61 is disengageably engaged with the rack portion 30 so as to hold the first clamping plate 3 in position. The board 60 includes a plurality of guide rails 63 and the sleeve 22 has a plurality of rails 222 which are movably engaged along the guide rails 63 so as to guide the movement of the sleeve 22. A pushing rod 62 is pivotably connected to the board 60 and includes an end contacting the pawl member 61 so that the pawl member 61 is removed from the rack portion 30 by pivoting the pushing rod 62 in direction 62a as shown in FIG. 4.

While we have shown and described the embodiment in accordance with the present invention, it should be clear to those skilled in the art that further embodiments may be made without departing from the scope of the present invention.

What is claimed is:

1. An air refresher holding device comprising:
   an air refresher;
   a sliding mechanism comprising a gear and a sleeve which has teeth matched with the gear, the sleeve being moved by rotating the gear;
   a first clamping plate having a rack portion on a side thereof and a pawl member disengageably engaged with the rack portion so as to hold the first clamping plate in position;
   a base having a first receiving portion defined in an end thereof and a path defined in an interior of the base, the air refresher received in the first receiving portion and the sliding mechanism received in the path, a plurality of first holes defined through the base, the path located being extended to a position where the first holes are defined; and
   a cover mounted to the base and having a second receiving portion which is located in alignment with the first receiving portion such that the air refresher is received therein, a plurality of second holes, a second clamping plate connected to a side of the cover and located in opposite to the first clamping plate.

2. The device as claimed in claim 1, wherein a pushing rod that comprises an end contacting the pawl member that is removed from the rack portion by pivoting the pushing rod.

3. The device as claimed in claim 1, wherein the first clamping plate has a chamber and the cover has a stop wall, a spring having an end received in the chamber and the other end of the spring contacting against the stop wall.

4. The device as claimed in claim 1, wherein the cover comprises a block and the first clamping plate comprises a slot in which the block is slidably engaged.

5. The device as claimed in claim 1 further comprising a fan located between the base and the cover, the first holes and the second holes located on two sides of the fan.

6. The device as claimed in claim 1, wherein a plurality of third holes are defined through the base and located beside the path.

7. The device as claimed in claim 1, wherein the cover has a support member located on an end thereof.

8. The device as claimed in claim 1, wherein the air refresher comprises two ridges on two sides thereof and two grooves are respectively defined in two insides of the first and second receiving portions, the ridges engaged with the grooves.

9. The device as claimed in claim 1, wherein the pawl member is integrally connected to a board that has a protrusion to which a center of the gear is connected.

10. The device as claimed in claim 9, wherein the board includes a plurality of guide rails and the sleeve has a plurality of rails that are movably engaged along the guide rails.

* * * * *